(12) United States Patent
Poehlmann et al.

(10) Patent No.: US 9,347,060 B2
(45) Date of Patent: May 24, 2016

(54) BIOLOGICALLY ACTIVE MOLECULES, PARTICULARLY BASED ON PNA AND SIRNA, METHOD FOR THE CELL-SPECIFIC ACTIVATION THEREOF, AND APPLICATION KIT TO BE ADMINISTERED

(75) Inventors: Tobias Poehlmann, Jena (DE); Lydia Seyfarth, Jena (DE)

(73) Assignee: Friedrich-Schiller-Universitaet Jena, Jena (DE)

( * ) Notice: Subject to any disclaimer, the term of this patent is extended or adjusted under 35 U.S.C. 154(b) by 30 days.

(21) Appl. No.: 12/449,419

(22) PCT Filed: Feb. 13, 2008

(86) PCT No.: PCT/DE2008/000279
§ 371 (c)(1),
(2), (4) Date: Aug. 6, 2009

(87) PCT Pub. No.: WO2008/098569
PCT Pub. Date: Aug. 21, 2008

(65) Prior Publication Data
US 2010/0009446 A1    Jan. 14, 2010

(30) Foreign Application Priority Data
Feb. 15, 2007  (DE) .......................... 10 2007 008 596

(51) Int. Cl.
*C07H 21/04*    (2006.01)
*C12N 15/11*    (2006.01)
*C12N 15/113*   (2010.01)

(52) U.S. Cl.
CPC ............ *C12N 15/111* (2013.01); *C12N 15/113* (2013.01); *C12N 2310/14* (2013.01); *C12N 2310/3181* (2013.01); *C12N 2310/3513* (2013.01); *C12N 2320/32* (2013.01)

(58) Field of Classification Search
None
See application file for complete search history.

(56) References Cited

U.S. PATENT DOCUMENTS

| | | | |
|---|---|---|---|
| 5,898,031 A | 4/1999 | Crooke | |
| 6,107,094 A | 8/2000 | Crooke | |
| 6,506,559 B1 | 1/2003 | Fire et al. | |
| 7,056,704 B2 | 6/2006 | Tuschl et al. | |
| 7,098,002 B1 * | 8/2006 | Rubinstein et al. | 435/69.1 |
| 2003/0219375 A1 * | 11/2003 | Piwnica-Worms | 424/1.11 |
| 2008/0234183 A1 * | 9/2008 | Hallbrink et al. | 514/12 |
| 2010/0009446 A1 | 1/2010 | Poehlmann et al. | |

FOREIGN PATENT DOCUMENTS

| | | |
|---|---|---|
| WO | WO-2006/019430 | 2/2006 |
| WO | WO-2007/056153 | 5/2007 |
| WO | WO-2007/069068 | 6/2007 |

OTHER PUBLICATIONS

Jan. 1, 2004, Cancer siRNA therapy by tumor selective delivery with ligand-targeted sterically stabilized nanoparticle, Raymond M. Schiffelers, et al., Nucleic Acids Research, vol. 32, No. 19, pp. 1-10.
Jan. 1, 2006 Antibody-directed cell-type-specific delivery of siRNA, Hans-Peter Vornlocher, Trends in Molecular Medicine, vol. 12, No. 1, pp. 1-3.
Dec. 21, 2004, Tumor imaging by means of proteolytic activation of cell-penetrating peptides, T. Jiang et al., Proceedings of the National Academy of Sciences of USA, vol. 101, No. 51, pp. 17867-17872.
Jan. 2007, Development of a novel systemic gene delivery system for cancer therapy with a tumor-specific cleavable PEG-lipid, H. Hatakeyama et al., Gene Therapy, vol. 14, No. 1, pp. 68-77.
Sep. 2006 Protease-Modulated Cellular Uptake of Quantum Dots, Yan Zhang et al., Nano Letters vol. 6, No. 9, pp. 1-9.
Nov. 1, 2002 "Antitumor Effect of in Vivo Somatostatin Receptor Subtype 2 Gene Transfer in Primary and Metastatic Pancreatic Cancer Models." F. Vernejoul et al. Cancer Research. vol. 62 pp. 6124-6131.
Aug. 2006 "Ligand-Targeted Delivery of Therapeutic siRNA." Ikeda et al., Pharmaceutical Research. vol. 23, No. 8, pp. 1631-1640.
Jan. 30, 2006 "Light controllable siRNAs regulate gene suppression and phenotypes in cells." Q. N. Nguyen et al. Biochimica et Biophysica Acta. vol. 1758 pp. 394-403.
Apr. 2006 "Delivery Strategies for siRNA-mediated Gene Silencing." I.R. Gilmore et al. Current Drug Delivery. vol. 3, No. 2, pp. 147-155.
Jun. 2004 "Downregulation Enhanced Green Fluorescence Protein Gene Expression by RNA Interference in Mammalian Cells." M. Zhang et al. RNA Biology. vol. 1, pp. 74-77.
May 24, 2001 "Duplexes of 21-nucleotide RNAs mediate RNA interference in cultured mammalian cells." S. M. Elbashir et al. Nature. vol. 411, pp. 494-498.
2004 "Efficient and Isoform-Selective Inhibition of Cellular Gene Expression by Peptide Nucleic Acids." Y. Liu et al. Biochemistry. vol. 43, pp. 1921-1927.
Jun. 2005 "Activity of Stabilized Short Interfering RNA in a Mouse Model of Hepatitis B Virus Replication." D. V. Morrissey et al. Hepatology. pp. 1349-1356.
B Urban-Klein, et al.; "RNAi-mediated gene-targeting through systemic application of polyethylenimine (PEI)-complexed siRNA in vivo", Gene Ther, 12 (5), 2005, pp. 461-466.

(Continued)

*Primary Examiner* — Kimberly Chong
(74) *Attorney, Agent, or Firm* — Jordan and Hamburg LLP

(57) ABSTRACT

Biologically active molecules are inactivated for selective activation by target cells by being covalently bonded to one or more peptides each of which has one or more specific amino acid sequences that are selected in respect of enzymes cell-specific for target cells. The bonds, which are broken exclusively by the enzymes cell-specific for the target cells in order to biologically activate the molecules, allow the molecules to remain biologically inactive in cells other than the target cells. The molecules are used for influencing gene expression of preferably sick and infected organs or cells, for example.

28 Claims, 4 Drawing Sheets

(56) References Cited

OTHER PUBLICATIONS

Figure 1:
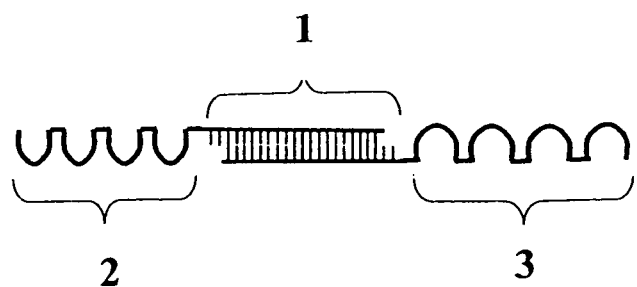
Figure 1:
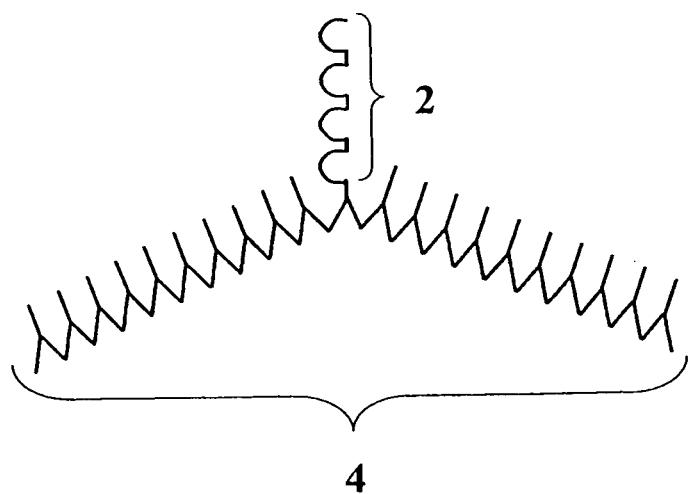

David V. Morrissey, et al.; "Potent and persistent in vivo anti-HBV activity of chemically modified siRNAs", Nature Biotechnology, vol. 23, No. 8, Aug. 2005, pp. 1002-1007.
May 15, 1991 Netzel-Arnett S et al: "Continously recording fluorescent assays optimized for five human matrix metalloproteinases", Analytical Biochemistry, Bd. 195, Nr. 1, May 15, 1991, Seiten 86-92, XP024828075.
Jul. 1, 2001 Turk B E et al: "Determination of protease cleavage site motifs using mixture-based oriented peptide libraries", Nature Biotechnology, Bd. 19, Nr. 7, Jul. 1, 2001, Seiten 661-667, XP002254824.
Apr. 1, 2003 Harborth J et al: "Sequence, chemical, and structural variation of small interfering RNAs and short hairpin RNAs and the effect on mammalian gene silencing", Antisense & Nucleic Acid Drug Development, Bd. 13, Nr. 2, Apr. 1, 2003, Seiten 85-105, XP002284355.
Sep. 1, 2002 Schwarz D S et al: "Evidence That Sirnas Function as Guides, Not Primers, in the Drosophila and Human RNAI Pathways", Molecular Cell, Bd. 10, Nr. 3, Sep. 1, 2002, Seiten 537-548, XP009019083.
Makoto Hayakari et al., "A Rapid Simple Spectrophotometric Assay of Angiotensin-Converting Enzyme", Analytical Biochemistry 84, pp. 361-369 (1978).
S. Shah et al., "Tolerance of RNA interference toward modifications of the 5' antisense phosphate of small interfering RNA", Oligonucleotides 2007 Spring'17(1) pp. 35-43 Abstract.

* cited by examiner a)

b)

SEQUENCE LISTING

<160> NUMBER OF SEQ ID NOS: 11

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Leu Glu Val Asp
1

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Leu Ala Leu Trp Ala Arg
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Dpa

<400> SEQUENCE: 3

Pro Leu Gly Leu Xaa Ala Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Pro Leu Gly Met Trp Ser Arg
1               5

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Nval

<400> SEQUENCE: 5

Arg Pro Lys Pro Tyr Ala Xaa Trp Met Lys
1               5                   10

```
<210> SEQ ID NO 6
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phe(p-nitro)

<400> SEQUENCE: 6

Phe Arg Phe
1

<210> SEQ ID NO 7
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Ala Phe
1

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Gly Phe Phe Leu
1               5

<210> SEQ ID NO 9
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly His Leu
1

<210> SEQ ID NO 10
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Phe Gly Gly
1

<210> SEQ ID NO 11
<211> LENGTH: 3
<212> TYPE: PRT
```

-continued

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: p-Nitro-Phe

<400> SEQUENCE: 11

Gly Phe Pro
1
```

BIOLOGICALLY ACTIVE MOLECULES, PARTICULARLY BASED ON PNA AND SIRNA, METHOD FOR THE CELL-SPECIFIC ACTIVATION THEREOF, AND APPLICATION KIT TO BE ADMINISTERED

BACKGROUND OF THE INVENTION

The invention relates to special biologically active molecules, particularly based on peptide nucleic acids (PNA) and short interfering RNA (siRNA), a method for their transfection into a target cell and cell-specific activation in this cell or directly before their transfection, and an application kit to be administered in combination with a transfection system. Said biologically active molecules interact with the mRNA of the target gene and in the case of siRNA they form together with specific endoribonucleases an RNA protein complex named RISC (RNA induced silencing complex). The RISC complex bonds to the target mRNA and endonucleases restrict the target mRNA. In this way, gene expression is suppressed and consequently the formation of target proteins is inhibited. If activated PNA molecules are used, the translation will be prevented due to the bonding to the target mRNA.

The cell-specifically activatable, biologically active molecules can be used, for example, for combating abnormal cells and inhibiting their growth, particularly in tumor treatment, treatment of virus infections, and age-specific treatments for example. Generally, the cell-specifically activatable, biologically active molecules can be used for the modulation of gene expression of the target cells. This modulation does not only allow reduction of the gene expression but also increase thereof by achieving a reduction of the expression of the negative regulators of the target gene by means of the biologically active molecules.

The inhibition of gene expression by introducing short (19-23 bp), double-stranded RNA molecules (siRNA) or PNA molecules in eukaryotic cells, which is specific for a sequence segment of the mRNA of a target gene, has already been described (Elbashir S M et al.: Duplexes of 21-nucleotide RNAs mediate RNA interference in cultured mammalian cells, Nature, 2001 May 24, 411(6836), 494-8; Liu Y et al.: Efficient and isoform-selective inhibition of cellular gene expression by peptide nucleic acids, Biochemistry, 2004 Feb. 24, 43(7), 1921-7; U.S. Pat. No. 5,898,031; U.S. Pat. No. 7,056,704).

The use of such molecules does not prevent the reading of a gene and the generation of an mRNA, but in the case of siRNA it initiates an endogenous mechanism that degrades the target mRNA. Finally, as written above, the formation of a specific protein is suppressed without impairing the expression of further genes (post-transcriptional gene silencing).

To suppress the expression of a gene, the siRNA and PNA molecules can be directly introduced into the cell, particularly via transfection reagents and electroporation (Zhang M et al.: Downregulation enhanced green fluorescent protein gene expression by RNA interference in mammalian cells, RNA Biol. 2004 May, 1(1), 74-7; Gilmore I R et al.: Delivery strategies for siRNA-mediated gene silencing, Epub 2004 May 22., Curr Drug Deliv. 2006 Apr. 3(2), 147-5; U.S. Pat. No. 6,506,559).

The disadvantage of this method is the relative instability of the siRNA but it can be reduced by chemical modifications (U.S. Pat. No. 6,107,094).

A particular problem for the therapeutic application of biologically active molecules is an application in vivo. Methods for stabilizing the siRNA have been developed for such an application in order to reduce the degradation (Morrissey et. al.: Chemical Modifications of Synthetic siRNA, Pharmaceutical Discovery, May 1, 2005), and transfection reagents have been engineered, for example nanoparticles, in vivo-jetPEI™ (Polyplus), that introduce the siRNA into the cells in vivo, too (Vernejoul et al.: Antitumor effect of in vivo somatostatin receptor subtype 2 gene transfer in primary and metastatic pancreatic cancer models, Cancer Research 62, 2002, 6124-31; Urban-Klein B, Werth S, Abuharbeid S, Czubayko F, Aigner A: RNAi-mediated gene-targeting through systemic application of polyethylenimine (PEI)-complexed siRNA in vivo, Gene Ther 12(5), 2005, 461-6.).

Furthermore, methods have been evolved to increasingly transfect siRNA into cells of a target tissue in vivo (Ikeda et. al.: Ligand-Targeted Delivery of Therapeutic siRNA, Pharmaceutical Research, Vol. 23, No. 8, August 2006).

However, the administration of biologically active substances in vivo is often problematic due to the systemic effect. The selective introduction of these substances into target cells is not sufficiently specific. This disadvantage is particularly important for siRNA and PNA molecules that shall selectively act and shall have this selective effect only in the target cells. The cell specificity achieved by transfection reagents that are provided with a tissue or cell marker (e.g. antibody/antigen-marked nanoparticles, TAT protein flanking and others) is not sufficiently high. Wrong transfection is the result.

Moreover, a method is known that deactivates the biological effect of siRNA molecules by bonding fluorochromes and bringing back said molecules to their active state by exposing them to light of a defined wave length (Q N Nguyen et al.: Light controllable siRNAs regulate gene suppression and phenotypes in cells, Biochim Biophys Acta, 2006). This activation is initiated from the outside and is not cell-specific in any way. After their activation said siRNA molecules have consequently an undesired effect in all the other transfected cells, too and not only in the target cells as intended.

Furthermore, it is also difficult to use this mechanism for in vivo applications.

SUMMARY OF THE INVENTION

The aim of the invention is to produce biologically active substances that can be transfected into a target cell both in vitro and in vivo and inhibit gene expression exclusively here without influencing the substance-specific expression of the target gene and thus the formation of protein in other cells of the organism.

For the treatment of tumors, which has been mentioned as a possible application, this method shall selectively suppress the expression of the target gene and thus the protein formation in tumor cells without influencing healthy cells—which can also be reached by the active substances—and their continued existence.

Said aim is achieved by a covalent bond of the biologically active molecules, particularly PNA and siRNA, to one or more peptides each of which has at least one specific amino acid sequence that is selected in respect of enzymes typical of the target cells and is significant for the covalent bond and its breaking. Said covalent bond deactivates the biologically active molecules. Therefore, a specific gene expression is not inhibited after the transfection in cells as long as even only one of the bonded peptide chains remains at the PNA or siRNA molecules due to the non-existence of the corresponding enzyme typical of the target cell. By an appropriate transfection system, for example nanoparticles or coat molecules such as liposomes, the deactivated substance molecules can be transfected into the target cells. Here, said deactivating covalent bonds are broken in a cell-typical manner by the one or more cell-specific enzymes relevant for the amino acid sequences of the one or more coupling peptides. Thus, the biological strength of the molecule that is now within the target cell and separated from peptides is activated. As a result, the molecule bonds to the specific mRNA of the target cell and inhibits the gene expression in this special cell in the manner as such.

Figure 4:
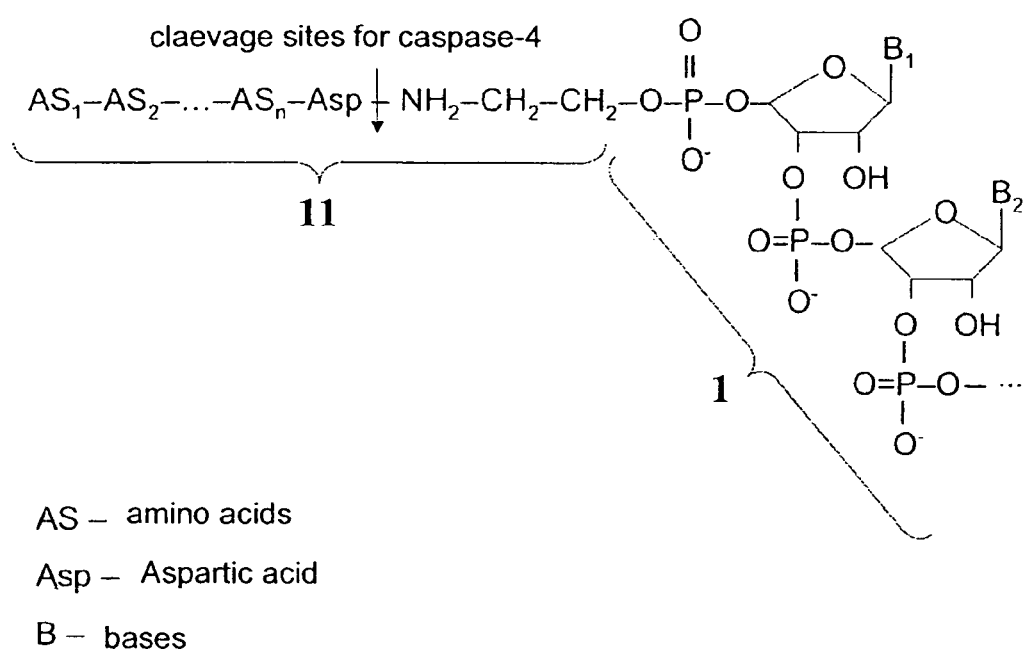

Unlike in the predefined target cells, in all other cells of the organism that can also be reached by the molecules said molecules remain inactive because the covalent bonds between the biologically active molecule, in particular PNA and siRNA, and the one or more peptides persist completely (no peptide bond has been broken) or partly (not all peptide bonds have been broken) because of the non-existence of the target enzyme or enzymes typical of the target cell. Due to the continuing covalent peptide bond the biologically active molecule does not form a bond with the mRNA of this cell and, if siRNA is used, a RISC will not be initiated.

Even though the inventive molecule constructs that are to be transfected in their unbound form, for example in a tumor treatment, do not only get to or at a tumor target cell but can also reach healthy cells (what is hardly to be avoided in practice) said molecule will be activated selectively and exclusively in or at the tumor target cells by the cell-specific enzyme present here and the substance-related expression of the target gene will be suppressed. Although the molecule constructs are present in the not sick (or for the intended biological effect not purposive) cells gene expression and thus protein formation for the continuing existence of the healthy cells remain unaffected from this substance because said molecule constructs are permanently inactive.

It is also possible that even directly before the transfection of the one or more covalent bonds into the target cell each of said bonds is activated partly or completely (referring to the total number of covalent peptide bonds) by one or more cell-specific enzymes being on the surface or in the vicinity of the target cell.

For example, several peptide chains with amino acid sequences individually selected for the different enzymes of the target cell could exist and each of one or more bonds is already broken directly on the surface or in the vicinity of the target cell.

It is also conceivable that the biologically active molecules in their inactive state, which is caused by said peptide bonds, get to the target cells or the target tissue and there they are completely activated before their transfection into the target cell, particularly if they cannot reach other cells in this part of the organism.

Thanks to the proposed highly selective effect of the molecules as a result of the target-cell-enzyme-specific inactivity/activity the biologically inactive molecule constructs to be transfected can be administered systemically, if an appropriate peptide bond (with defined amino acid combinations) is formed.

The molecule constructs can be bonded in or to the target cells to ensure a better transport or to other substances (for example nanoparticles as a carrier system) to ensure the stability of said molecule constructs.

Moreover, well-known mechanisms that increase the tissue or cell selectivity (for example ligand/antibody/antigen-marked nanoparticles, TAT protein flanking) can be used to increase the transfection rate. The combination with these known mechanisms complements the described invention and leads to a reduction of the amount of the inventive substance due to the pre-selection of the target cells. This advantage results from the fact that the active substance mostly reaches cells in tissue with a good blood flow when it is transfected in vivo into the blood circulation. The proposed molecules with the inventive biologically deactivating bond to one or more peptides can be very well used in combination with generally known transfection systems, such as nanoparticles with or without ligand/antibody/antigen marking, with coating nanoparticles or lipids and lipid-based transfection methods. Depending on the intended application, such transfection systems themselves already decrease organism-caused wrong transfections and therefore, considered in relation, an increased number of cells is transfected into the target tissue so that the amount of substance to be used can be limited to a minimum.

If this invention is applied, the wrong transfections cannot be actually inhibited but the wrongly transfected molecules are not biologically active in the cells other than the target cells, even though they are still undesired in them. The inactive form of the molecules also remains unchanged despite the inventive molecule activation in or at the target cells so that the biological effect of the molecules is only active in the target cells and a highly cell-selective modulation of gene expression is reached, unlike in different mechanisms known so far.

The invention is not limited to applications for treating tumors and, for example, cells infected by viruses (e.g. HIV). The inventive molecule constructs can be used for all clinical syndromes that are based on an increased or reduced gene expression in order to treat the disease itself or its symptoms. Furthermore, age- or development-specific changes in the gene expression pattern of cells can be treated. Additionally, the invention can be used for all applications in vitro or in vivo that aim at the selective change in gene expression in specific cells.

It is advantageous to use an application kit that provides the biologically active molecules with the bonded peptides that have—as proposed—amino acid sequences selected in respect of enzymes typical of the target cells and an appropriate transfection system as well as other additives. The application kit contains all required substances and a manual to instruct the user about the intended operation.

BRIEF DESCRIPTION OF THE DRAWINGS

In the following, examples explain the invention in detail in schematic drawings.

They show:

FIG. 1: general structure of the inventive cell-specific activatable molecule constructs (deactivated state; due to a changed space structure of the molecules the formation of the RISC is suppressed in example a) and in example b) the bond to the mRNA is prevented)

a) example for siRNA with two bonded peptides
b) example for PNA with one bonded peptide FIG. 2: example for a siRNA molecule construct bonded to a transfection system for the transfection into the target cells a) biologically inactive molecule construct for the transfection into the target cell
b) bond breakage by the enzyme typical of the target cell
c) molecule biologically activated in or at the target cell with broken bond between the siRNA and the peptide FIG. 3: siRNA molecule construct with two peptide bonds and one transfection system for the transfection into the target cells a) molecule construct with peptide bonds
b) breakage of the peptide bonds by different enzymes of the target cell FIG. 4: representation of an exemplary bond between a peptide and an siRNA; in this case a possible enzyme for decomposing the peptide bond is Caspase-4

DETAILED DESCRIPTION OF THE INVENTION

FIG. 1 shows the general structure of the inventive cell-specific activatable molecule constructs in a deactivated state as an example for siRNA (FIG. 1a) and for PNA (FIG. 1b).

In FIG. 1a, a siRNA 1 as a biologically active molecule is bonded to two peptides 2, 3. Due to these bonds on both sides the siRNA 1 is biologically inactive and is transfected into a target cell (not shown for the sake of clarity).

FIG. 1b demonstrates how a PNA 4 instead of the siRNA 1 is bonded as a biologically active molecule to the peptide 2 and is thus also biologically deactivated for the transfection.

Figure 2:
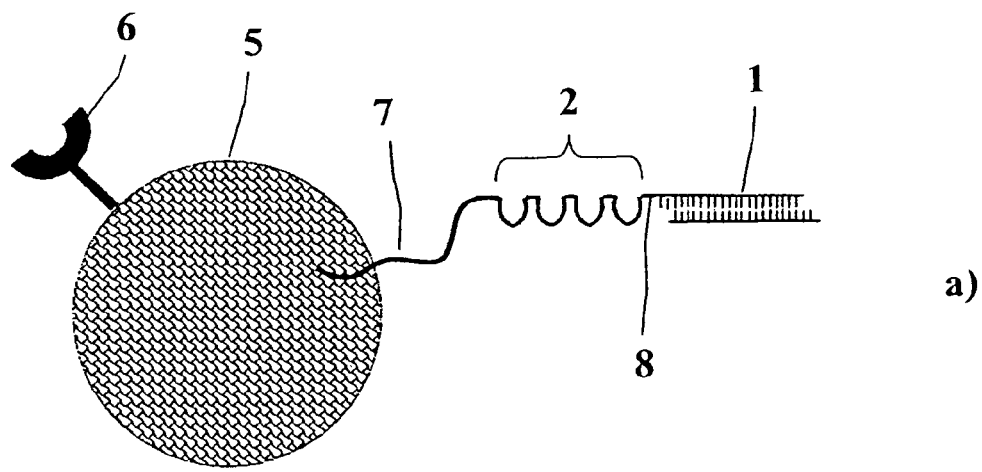
Figure 2:
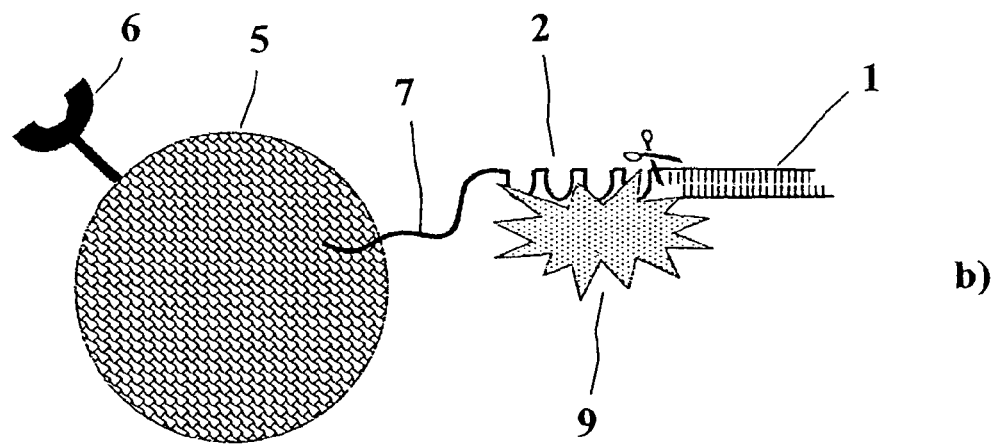
Figure 2:
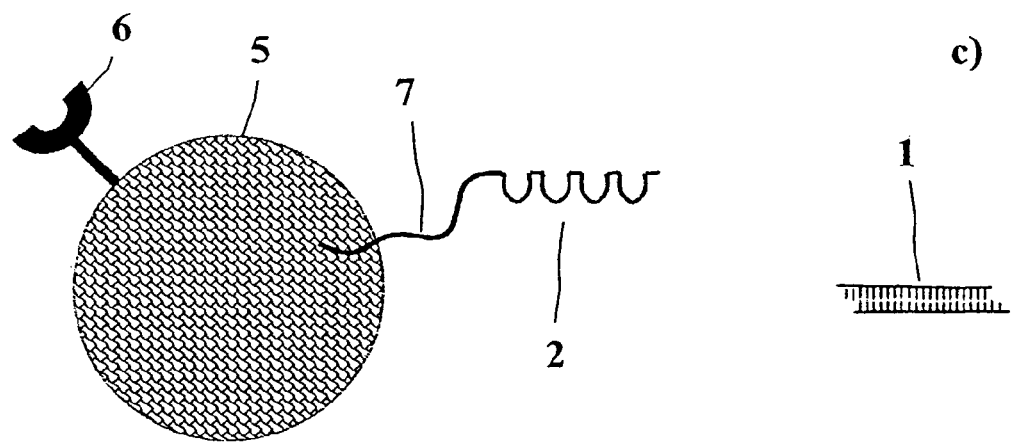

FIG. 2 shows a possible construct that could be used for the transfection of the molecule (siRNA 1), which is biologically deactivated by the peptide (peptide 2), into one target cell. And (FIG. 2a) to a nanoparticle 5 antibodies 6 could be bonded for the semi-selective bonding to target cells and polyethylene glycol chains (PEG) 7 for anchoring the peptide 2 and the siRNA 1.

Furthermore, the bonding between the siRNA 1 and the deactivating peptide 2 is shown as an restricting site 8 for the breakage by a selectively restricting enzyme 9 typical of the target cell (FIG. 2). This enzyme 9, which is only present in or at the aforesaid (not shown) target cell, breaks the peptide bond of the siRNA 1 at the restricting site 8 due to the specific amino acid sequence (FIG. 2c). The molecule (siRNA 1) that is again biologically active now because of the broken peptide bond and the residual construct consisting of the nanoparticle 5, the antibody 6, the polyethylene glycol chains (PEG) 7 and the peptide removed from the siRNA 1 are consequently separated.

According to the invention the peptide bond of the siRNA 1 at the restricting site 8 still exists in or at other cells of the organism that do not belong to the intended target cells and that are also reached by the biologically inactive molecule construct (see FIGS. 2a and 2b) by transfection and in or at which the enzyme 9 typical of the target cell is not present. The siRNA 1 as a biologically active molecule continues to be inactive (cp. FIG. 2a). The biological effect of the siRNA 1 desired in the target cells is suppressed in other cells by the unbroken restricting site 8.

Figure 3:
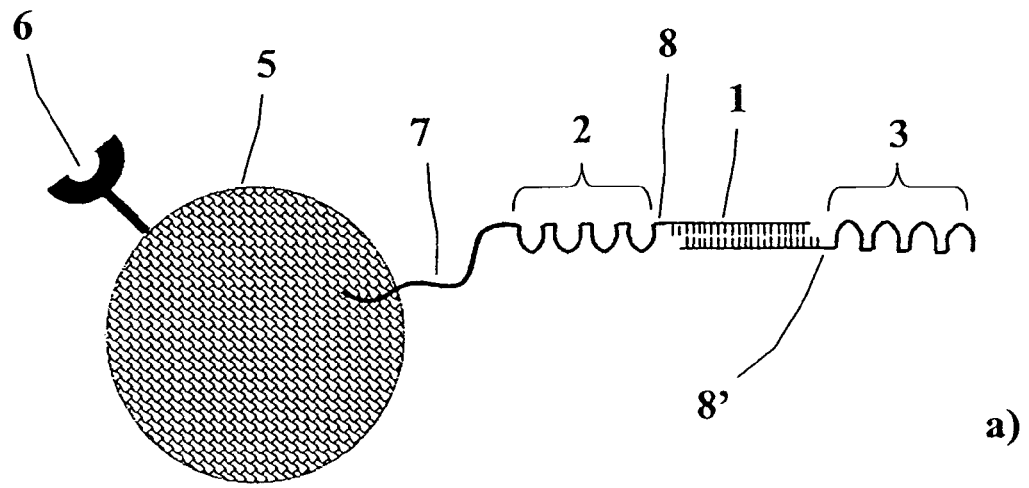
Figure 3:
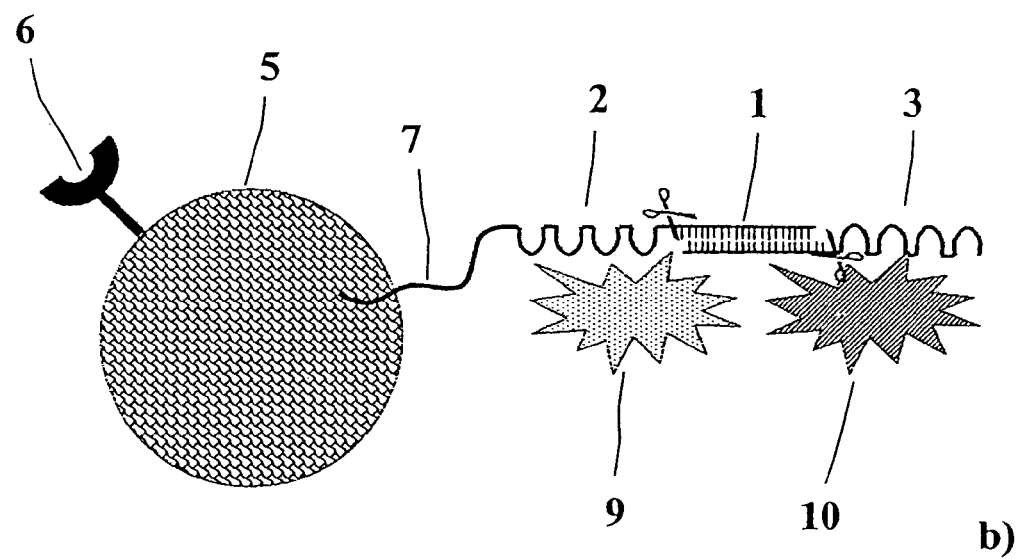

FIG. 3a shows an extension of the construct of FIG. 2. Here, a peptide 2, 3 is also bonded to different points of the siRNA 1 in order to deactivate its biological effect (cp. FIG. 1a). The different amino acid sequences in the peptides 2, 3 are selected so that two specific enzymes (exclusively) present in or at the target cell can break the peptide bonds of these restricting sites 8 or 8'. If even only one of the two peptides 2, 3 is not present at a cell that is also reached by the construct according to FIG. 3a (e.g. after a wrong transfection) but does not belong to the target cells, at least one of the two peptide bonds persists at the restricting site 8 or 8' due to the missing of the equivalent enzyme 9, 10 typical of the target cell. The siRNA 1 will even continue to be inactive, if only a single peptide bond still exists. Only at the target cell in or at which the enzymes 9, 10 break the two restricting sites 8, 8' (sketched out in FIG. 3b) by the above mentioned defined amino acid sequences of the peptides 2, 3, the siRNA 1 will be separated from the rest of the molecule construct (cp. also FIG. 2c). Thus, the siRNA 1 as a biologically active molecule can only develop its intended effect by the transfection into this target cell.

FIG. 4 shows a possible bond between the siRNA 1 and one peptide with one possible specific amino acid sequence 11 (amino acid sequence is -L-E-V-D-) demonstrated for a selectively separating enzyme Caspase-4 that is present in one target cell. Said enzyme would break the bond for the activation of the siRNA 1 at the separation point for Caspase-4 that is symbolized by the arrow and indicated in words.

In the illustrated example, a molecule rest would remain at the siRNA 1 after the aforesaid separation by the enzyme Caspase-4 but this would not impair the biological activity of siRNA 1.

The invention is not limited to the just indicated amino acid sequence (-L-E-V-D-) shown in FIG. 4 with respect to the breakage of the peptide bond at the siRNA 1 by means of the enzyme Caspase-4 typical of the target cell. The following table contains a list of examples of other amino acid sequences of the peptide that can be used for the proposed application for special target cell enzymes:

| Target cell enzyme | Amino acid sequence of the peptide |
|---|---|
| Matrix metalloproteinase-1 | -Pro-Leu-Ala-Leu-Trp-Ala-Arg- |
| Matrix metalloproteinases-2,7 | -Pro-Leu-Gly-Leu-Dpa-Ala-Arg- |
| Matrix metalloproteinases-2,9 | -Pro-Leu-Gly-Met-Trp-Ser-Arg- |
| Matrix metalloproteinases-3,1,2,9 | -Arg-Pro-Lys-Pro-Tyr-Ala-Nval-Trp-Met-Lys- |
| Cathepsin-S | -Phe-Arg-Phe(p-nitro)- |
| Cathepsin-G | -Ala-Ala-Phe- |
| Cathepsin-D | -Arg-Gly-Phe-Phe-Leu- |
| Angiotensin converting enzyme | -Gly-His-Leu- or -Phe-Gly-Gly- or -Gly-p-Nitro-Phe-Pro |

The four target cell enzymes listed first in the above table can also be present on the surface of the target cell or in its vicinity. In such a case and for such an application of the biologically active molecules said four target enzymes would be able to break the corresponding peptide bond by the inventively selected amino acid sequence even directly before the transfection into the target cell. This application will be particularly possible, for example for the transfection into a target cell complex, if the biologically active molecules, which have reached the range of the target cell in their inactive state, cannot get to other (non-desired) cells in this part of the organism after their complete or partial activation already performed outside the target cell.

It is advantageous to use an application kit that provides the required biologically active molecules with the bonded peptides that have—as proposed—amino acid sequences selected in respect of enzymes typical of the target cells. The application kit should contain all necessary substances in ampoules, purposefully also a selection of appropriate transaction systems (such as nanoparticles, ligands and polyethylene glycol) as well as one or several probes or syringes with hollow needles for the injection of the mixture of the contents of the ampoules into the medium of the target cells. The user can prepare and apply appropriate application mixtures and use them as described in a supplied instruction manual that contains a list of the selectable peptide amino acid sequences and the corresponding enzymes of the target cells (cp. Table above).

It would be favorable to prepare such an application kit specifically for selected target cells and target genes in accordance with the type of application (in vitro or in vivo).

The invention claimed is:

1. A biologically inactive molecule that is convertible to a biologically active molecule by a target cell in order to inhibit gene expression of the target cell, the biologically inactive molecule comprising a siRNA bonded to at least one peptide by at least one covalent bond, the at least one peptide including one or more amino acid sequences selected for one or more enzymes specific to the target cell and providing a site specific for cleavage by the one or more enzymes specific to the target cell, whereby after transfection of a plurality of biologically inactive molecules to cells of an organism that has target cells and non-target cells, the one or more enzymes specific to the target cells break within the cells the covalent bond to convert the biologically inactive molecules into biologically active molecules, the at least one covalent bond only broken to convert the biologically inactive molecules into biologically active molecules by the one or more enzymes specific to the target cells, whereby the biologically active molecules inhibit gene expression of the target cells by binding to mRNA of the target cells and inducing RNA interference, and the biologically inactive molecules remain inactive in non-target cells that do not produce one or more enzymes that can break the covalent bond to effect biological activation of the biologically inactive molecules.

2. The biologically inactive molecule according to claim 1, wherein the at least one peptide has an amino acid sequence -L-E-V-D- (SEQ ID NO: 1) for breaking the bond by the cell-specific enzyme Caspase-4.

3. The biologically inactive molecule according to claim 1, wherein the at least one peptide contains an amino acid sequence -Phe-Arg-Phe(p-nitro)- (SEQ ID NO: 6) for breaking the bond by the cell-specific enzyme Cathepsin-S.

4. The biologically inactive molecule according to claim 1, wherein the at least one peptide contains an amino acid sequence -Ala-Ala-Phe- (SEQ ID NO: 7) for breaking the bond by the cell-specific enzyme Cathepsin-G.

5. The biologically inactive molecule according to claim 1, wherein the at least one peptide contains an amino acid sequence -Arg-Gly-Phe-Phe-Leu- (SEQ ID NO: 8) for breaking the bond by the cell-specific enzyme Cathepsin-D.

6. The biologically inactive molecule according to claim 1, wherein the at least one peptide contains an amino acid sequence -Gly-His-Leu- (SEQ ID NO: 9) for breaking the bond by the cell-specific enzyme angiotensin-converting enzyme.

7. The biologically inactive molecule according to claim 1, wherein the at least one peptide contains an amino acid sequence -Phe-Gly-Gly- (SEQ ID NO: 10) for breaking the bond by the cell-specific enzyme angiotensin-converting enzyme.

8. The biologically inactive molecule according to claim 1, wherein the at least one peptide contains an amino acid sequence -Gly-p-Nitro-Phe-Pro- (SEQ ID NO: 11) for breaking the bond by the cell-specific enzyme angiotensin-converting enzyme.

9. A method for inhibiting gene expression of a target cell, comprising transfecting a plurality of biologically inactive molecules of claim 1 to an organism comprising target cells and non-target cells, whereby one or more enzymes specific to the target cells break within the cells the covalent bond to convert the biologically inactive molecules into biologically active molecules, the at least one covalent bond only broken to convert the biologically inactive molecules into biologically active molecules by the one or more enzymes specific to the target cells, whereby the biologically active molecules inhibit gene expression of the target cells by binding to mRNA of the target cells and inducing RNA interference, and the biologically inactive molecules remain inactive in non-target cells that do not produce one or more enzymes that can break the covalent bond to effect biological activation of the biologically inactive molecules.

10. The method according to claim 9, further comprising transfecting the plurality of biologically inactive molecules with a carrier.

11. The method according to claim 10, wherein the plurality of biologically inactive molecules are provided as a covering on the carrier, the carrier comprising nanoparticles or lipids.

12. The method according to claim 11, wherein the carrier comprises lipids.

13. The method according to claim 9, wherein the plurality of biologically inactive molecules are partly or completely, with respect to the total number of the covalent peptide bonds, activated before the transfection into the target cell by one or more of the cell-specific enzymes being present on the surface of or vicinity of the proximate to target cell.

14. The method according to claim 9, further comprising coupling the plurality of biologically active inactive molecules to one or more marker substances.

15. A kit for administering the biologically inactive molecule of claim 1 comprising
    a first ampoule comprising as ampoule contents a plurality of biologically inactive molecules of claim 1;
    a second ampoule comprising as ampoule contents a transfection medium;
    diluent and reaction buffers for the contents of the first, and second ampoules;
    at least one probe or syringe having a hollow needle provided for injecting a mixture of the contents of the first and second ampoules into a medium containing target cells; and
    an instruction manual containing a list of peptide amino sequences selectable for the corresponding cell-specific enzymes of the target cells.

16. The kit according to claim 15, further comprising at least one substance for semi-selective bonding of the plurality of biologically inactive molecules to the target cells.

17. The kit according to claim 15, further comprising at least one substance for anchoring the peptide and the plurality of biologically inactive molecules.

18. The kit according to claim 15, further comprising at least one substance for the transfection of the plurality of biologically inactive molecules into the target cell.

19. The biologically inactive molecule according to claim 1 comprising siRNA bonded to mRNA through a RISC complex.

20. The method according to claim 9, wherein the siRNA bonds to mRNA through a RISC complex.

21. The method according to claim 11, wherein the carrier comprises nanoparticles.

22. The method according to claim 13, wherein the cell-specific enzymes comprise at least one of matrix metalloproteinase-1, matrix metalloproteinases-2, matrix metalloproteinases-3, matrix metalloproteinases-7, or matrix metalloproteinases-9.

23. The kit according to claim 16, wherein the substance comprises antibodies.

24. The kit according to claim 17, wherein the substance includes polyethylene glycol chains.

25. A biologically inactive molecule that is convertible to a biologically active molecule by a target cell in order to inhibit gene expression of the target cell, the biologically inactive molecule comprising a PNA bonded to at least one peptide by at least one covalent bond, the at least one peptide including one or more amino acid sequences selected for one or more enzymes specific to the target cell and providing a site specific for cleavage by the one or more enzymes specific to the target cell, whereby after transfection of a plurality of biologically inactive molecules to cells of an organism that has target cells and non-target cells, the one or more enzymes specific to the target cells break within the cells the covalent bond to convert the biologically inactive molecules into biologically active molecules, the at least one covalent bond only broken to convert the biologically inactive molecules into biologically active molecules by the one or more enzymes specific to the target cells, whereby the biologically active molecules inhibit gene expression by binding to mRNA of the target cells and preventing its translation, and the biologically inactive molecules remain inactive in non-target cells that do not produce one or more enzymes that can break the covalent bond to effect biological activation.

26. A method for inhibiting gene expression of a target cell, comprising transfecting a plurality of biologically inactive molecules of claim 25 to an organism comprising target cells and non-target cells, whereby one or more enzymes specific to the target cells break within the cells the covalent bond to convert the biologically inactive molecules into biologically active molecules, the at least one covalent bond only broken to convert the biologically inactive molecules into biologically active molecules by the one or more enzymes specific to the target cells, whereby the biologically active molecules inhibit gene expression by binding to mRNA of the target cells and preventing its translation, and the biologically inactive molecules remain inactive in non-target cells that do not produce one or more enzymes that can break the covalent bond to effect biological activation of the biologically inactive molecules.

27. The method according to claim 26, wherein the PNA bonds to mRNA through a RISC complex.

28. A kit for administering the biologically inactive molecule of claim 25 comprising:
   a first ampoule comprising as ampoule contents a plurality of biologically inactive molecules of claim 25;
   a second ampoule comprising as ampoule contents a transfection medium;
   diluent and reaction buffers for the contents of the first, and second ampoules;
   at least one probe or syringe having a hollow needle provided for injecting a mixture of the contents of the first and second ampoules into a medium containing target cells; and
   an instruction manual containing a list of peptide amino sequences selectable for the corresponding cell-specific enzymes of the target cells.

\* \* \* \* \*